US009909994B2

United States Patent
Mishra et al.

(10) Patent No.: US 9,909,994 B2
(45) Date of Patent: Mar. 6, 2018

(54) METHOD AND AN ARRANGEMENT FOR MEASURING THE SMOOTHNESS OF GRAINS

(71) Applicant: Buhler (India) Pvt. Ltd., Attibele (IN)

(72) Inventors: Jyoti Prakash Mishra, Attibele (IN); Manit Kumar, Attibele (IN); Gopalakrishnan Trikkur, Attibele (IN); Bismillah Kani, Attibele (IN); Ye Aung, Yangon (MM)

(73) Assignee: Buhler (India) Pvt., Ltd., Attibele, Bangalore District (IN)

( * ) Notice: Subject to any disclaimer, the term of this patent is extended or adjusted under 35 U.S.C. 154(b) by 0 days.

(21) Appl. No.: 15/108,369

(22) PCT Filed: Feb. 24, 2014

(86) PCT No.: PCT/IN2014/000118
§ 371 (c)(1),
(2) Date: Jun. 27, 2016

(87) PCT Pub. No.: WO2015/102012
PCT Pub. Date: Jul. 9, 2015

(65) Prior Publication Data
US 2016/0327492 A1    Nov. 10, 2016

(30) Foreign Application Priority Data
Dec. 30, 2013 (IN) .......................... 6172/CHE/2013

(51) Int. Cl.
*G01B 11/30* (2006.01)
*G01N 21/85* (2006.01)
*G01N 33/10* (2006.01)

(52) U.S. Cl.
CPC .......... *G01N 21/85* (2013.01); *G01B 11/303* (2013.01); *G01N 33/10* (2013.01); *G01N 2021/8592* (2013.01)

(58) Field of Classification Search
CPC .......... G01N 2021/8592; G01N 21/85; G01N 33/10; G01B 11/303
(Continued)

(56) References Cited

U.S. PATENT DOCUMENTS 5,480,354 A    1/1996    Sadjadi

FOREIGN PATENT DOCUMENTS

| EP | 1 707 945 A1 | 10/2006 |
| EP | 1 830 176 A1 | 9/2007 |
| WO | WO 02/086473 A2 | 10/2002 |

OTHER PUBLICATIONS

International Search Reportprepared by the European Patent Office, acting as the International Searching Authority, for International Application PCT/IN2014/000118 dated Mar. 27, 2015.

*Primary Examiner* — Tri T Ton
(74) *Attorney, Agent, or Firm* — Haug Partners LLP

(57) ABSTRACT

The present invention relates to a method and an arrangement for measuring the smoothness of grains. In one embodiment, the arrangement includes a channel for supplying grains, especially rice grains, an obstacle arranged at the channel to slow down grains falling on the obstacle, so that the flow of grains forms a heap on the obstacle and an image capturing device placed facing the obstacle. The image capturing device is arranged to capture an image of the heap, where the area under the curve of the captured heap image indicates the degree of smoothness of the grains or the course of the curve of the captured heap image indicates the degree of smoothness of the grains.

12 Claims, 2 Drawing Sheets

(58) Field of Classification Search
USPC ..... 356/600–613, 237.1–237.6, 239.1–239.8
See application file for complete search history.

METHOD AND AN ARRANGEMENT FOR MEASURING THE SMOOTHNESS OF GRAINS

CROSS-REFERENCE TO RELATED APPLICATIONS

This application is the National Stage entry under 35 U.S.C. § 371 of International Application No. PCT/IN2014/000118 filed on Feb. 24, 2014, published on Jul. 9, 2015 under publication number WO 2015/102012 A1, which claims the benefit of priority under 35 U.S.C. § 119 of Indian Patent Application Number 6172/CHE/2013 filed Dec. 30, 2013.

FIELD OF THE INVENTION

The invention relates to an arrangement of measuring the smoothness of grains and a method for determining the smoothness of grains.

BACKGROUND OF THE INVENTION

The smoothness of polished grain, especially rice, is an important quality parameter in the grain milling industry. The obtained smooth surface is an expression of the achieved quality of the polishing. The assessment of the smoothness is commonly manually done based on touch and feel and underlies therefore the subjective perception of the respective assessor.

Generally, it is difficult to judge the quality of grain especially rice which is available in number of varieties which are different in quality, assessed e.g. as high grade or low grade quality. The assessment of quality, i.e. smoothness of rice, is determined based on personal judgment which requires at least two samples to be compared. In the absence of any methods that are supported from a scientific view point, the rice thus produced has often tended to be irregular in quality and this has often been the subject of concern.

Therefore there is a need in the art for a method to determine the smoothness of grains, especially rice grains, objectively.

SUMMARY OF THE INVENTION

According to an aspect the present invention pertains an arrangement for measuring the smoothness of grains, comprising a channel for supplying grains, especially rice grains, an obstacle arranged at the channel to slow down grains falling on the obstacle, so that the flow of grains forms a heap on the obstacle, an image capturing device placed facing the obstacle, wherein the image capturing device is arranged to capture an image of the heap, and wherein the area under the curve of the captured heap image indicates the degree of smoothness of the grains or wherein the course of the curve of the captured heap image indicates the degree of smoothness of the grains.

In the following the arrangement and method is to some extend described with focus on rice but is intended to be applicable for a wide range of grain sorts.

The obstacle being arranged in the flow of rice produces the effect that rice keeps laying on it when falling on the obstacle or being moved on the obstacle. This leads to a heap of rice laying on the obstacle. When this heap exceeds a certain height the rice grains will start sliding of the heap and falling down. The form and height of the heap that results from this process depends e.g. on the smoothness, size and humidity of the rice. Firstly it depends on the smoothness of the rice. Therefore a system model can be made comprising a dependency between the smoothness of the rice and the form of the heap on the obstacle.

The image capturing device takes a picture or several pictures at different times of that heap. The picture is taken e.g. from the side of the heap so that the acquired image shows a side elevation of the heap. The upper surface of the heap projects in the side elevation as curve. By the projection the 3D form of the heap is reduced to a 2D view comprising the curve that shows the upper surface of the heap. The area under the curve indicates the degree of smoothness of the grains. The form of the curve shows the degree of smoothness, too. If the curve has more steep sections it indicates less smoothness of the grains and if it has less steep sections it indicates more smoothness of the grains. So the smoothness can be determined by the arrangement assessing the steepness of sections of the curve. Further the average steepness of the course of the curve can be determined and the smoothness derived there from. A steeper course of the curve or steeper sections indicate less smoothness of the rice grains.

For determining the smoothness of the rice the arrangement is capable of analyzing the curve. The system model comprising the dependency between the curve and the degree of smoothness can be used for this analyzing. For example the area under the curve can be determined and be used to determine the degree of smoothness of the rice. As start and end point of the curve for determining the area under the curve the side points of the curve can be used which have the maximum distance to each other. For determining the area above a line between the points and the curve between these points can be used.

It is also possible to use the lateral contact points of the curve with the obstacle for that purpose. The area under the curve can then be determined as area which is determined by the curve between these two points and a direct connection line between these two points.

For any of these determination methods of the arrangement the system model can be used to determine the degree of smoothness from the area under curve. For this purpose the relevant data and constraints are represented in the system model.

According to an embodiment the obstacle has a discharge port, especially a hole, as outlet for the grains. This allows the rice collecting on the obstacle leaving the obstacle through the discharge port. By this measure the heap of rice can be steadily regenerated not only from the upper side with rice falling on it but also from the underside. Thus, if the smoothness of rice grains changes, the form of the heap adapts faster to the changed smoothness. This allows for a faster adaptation to changes of the smoothness of the rice. Further the accuracy of measurement of smoothness is improved, since less rice is left on the obstacle. The heap of rice is renewed faster and more complete.

It is possible to have the size of the discharge port changeable so that the velocity of discharging rice can be altered. This can be realized for example by restrictors. It is also possible to have more than one discharge port. One or several discharge ports can then be provided as partly or completely closable.

According to an embodiment the obstacle is formed as a vessel, especially as a hopper, for collecting the grains. This allows for building a very stable heap on the obstacle. The discharge port can then be built at the bottom of the vessel, especially the hopper. Further the obstacle as vessel allows for collecting more rice on the obstacle and therefore discharging rice from the heap without affecting the surface of the heap, i.e. the curve of the heap.

According to an embodiment the captured image of the heap is proportional to the degree of smoothness of the grains, the larger the area under the heap curve relate to lower degree of smoothness and the smaller the area under the heap curve relate to higher degree of smoothness. Smoother grains, e.g. rice grains, run more easily down the heap on the obstacle. Therefore smooth rice produces a heap on the obstacle that has less height than that of a heap built of less smooth rice.

According to an embodiment the image capturing device is a digital image capturing device. A digital image capturing device, e.g. a digital camera, provides a good integration in the digital processing of the picture of the heap. Further cheap standard solutions can be used.

According to an embodiment the arrangement further comprises a light source for radiating light on the grains, especially the grains lying on the obstacle. The light source can help improving the light conditions for capturing the image of the heap. Focused light can help realizing high contrast for capturing the image. The light source is e.g. a LED light source to minimize energy input into the grain by the light source. Preferably the light source has small outer dimensions making its integration easy.

According to an embodiment the arrangement further comprises a collecting element, especially a hopper, with a discharge port positioned above the obstacle. The collecting element enables it to supply the grain, especially rice, more controlled to the obstacle. For example, the collecting element can reduce the speed of falling down grains and prevent by this way to fast grains from elastic jumping of the obstacle or damaging the heap of grains on the obstacle. A hopper with a discharge port allows it to collect the grains and discharge them through a central discharge port. That has the advantage that the hopper covers an area under the hopper and can prevent grains directly falling on the obstacle in the covered area.

According to an embodiment the channel is built as a bypass of a main channel for conveying the grains. The bypass is for example built as channel connected to the main channel via an intake for grain and an outlet for grain. The obstacle is then arranged for example downstream of the intake and upstream of the outlet. The bypass allows it to bring the grain in a condition which is optimal for measuring the smoothness. The flow of grains in the bypass can be slower than that in the main channel. The flow of grains in the main channel can remain nearly unaffected. Therefore for measuring the smoothness of the grains the conveyor capacity of the main channel needs not be reduced.

A method for measuring the smoothness of grains, comprises the steps: supplying grains, especially rice grains, through a channel, slowing down falling down grains by an obstacle, so that the flow of grains forms a heap on the obstacle, capturing an image of the heap with an image capturing device; determining the area under the curve of the captured heap image, wherein the area of the curve is used to indicate the degree of smoothness of the grains, the larger area under the heap curve relate to lower degree of smoothness and the smaller the area under the heap curve relate to higher degree of smoothness or analyzing the form of the curve, wherein the course of the curve is used to indicate the degree of smoothness of the grains, more steep sections of the curve indicate a lower degree of smoothness and less steep sections indicate a higher degree of smoothness of the grain.

The arrangement and method for determining the smoothness of grains, especially rice grains, provides an objective assessment of the economic value and luster of polished rice grains. Further the method is fast and allows a continuous online quality assessment of the grains while the grains are conveyed. Quality variations of the grains can therefore immediately be detected and necessary steering measures of the grain polishing system can be taken. Therefore quality variations of the grains can be reduced and an improved grain quality can be delivered. That allows for a better marked value of the grain.

According to an embodiment the area covered by the curve is determined by a CPU connected to the image capturing device. The CPU carries out mathematical operations useful to determine for example the area under the curve or to extract and analyze form patterns of the curve. Further it is possible to have the arrangement connected to the control of a grain polishing device. This allows to adapt the polishing process based on the results of the smoothness or the grains. Further it is possible to automatically separate grains of different qualities based on the measurement of smoothness result.

BRIEF DESCRIPTION OF THE DRAWINGS

The above and other aspects, features, and advantages of certain exemplary embodiments of the present invention will be more apparent from the following description taken in conjunction with the accompanying drawings in which.

Persons skilled in the art will appreciate that elements in the figures are illustrated for simplicity and clarity and may have not been drawn to scale. For example, the dimensions of some of the elements in the figure may be exaggerated relative to other elements to help to improve understanding of various exemplary embodiments of the present disclosure.

Throughout the drawings, it should be noted that like reference numbers are used to depict the same or similar elements, features, and structures.

DETAIL DESCRIPTION OF THE DRAWINGS

Figure 1:
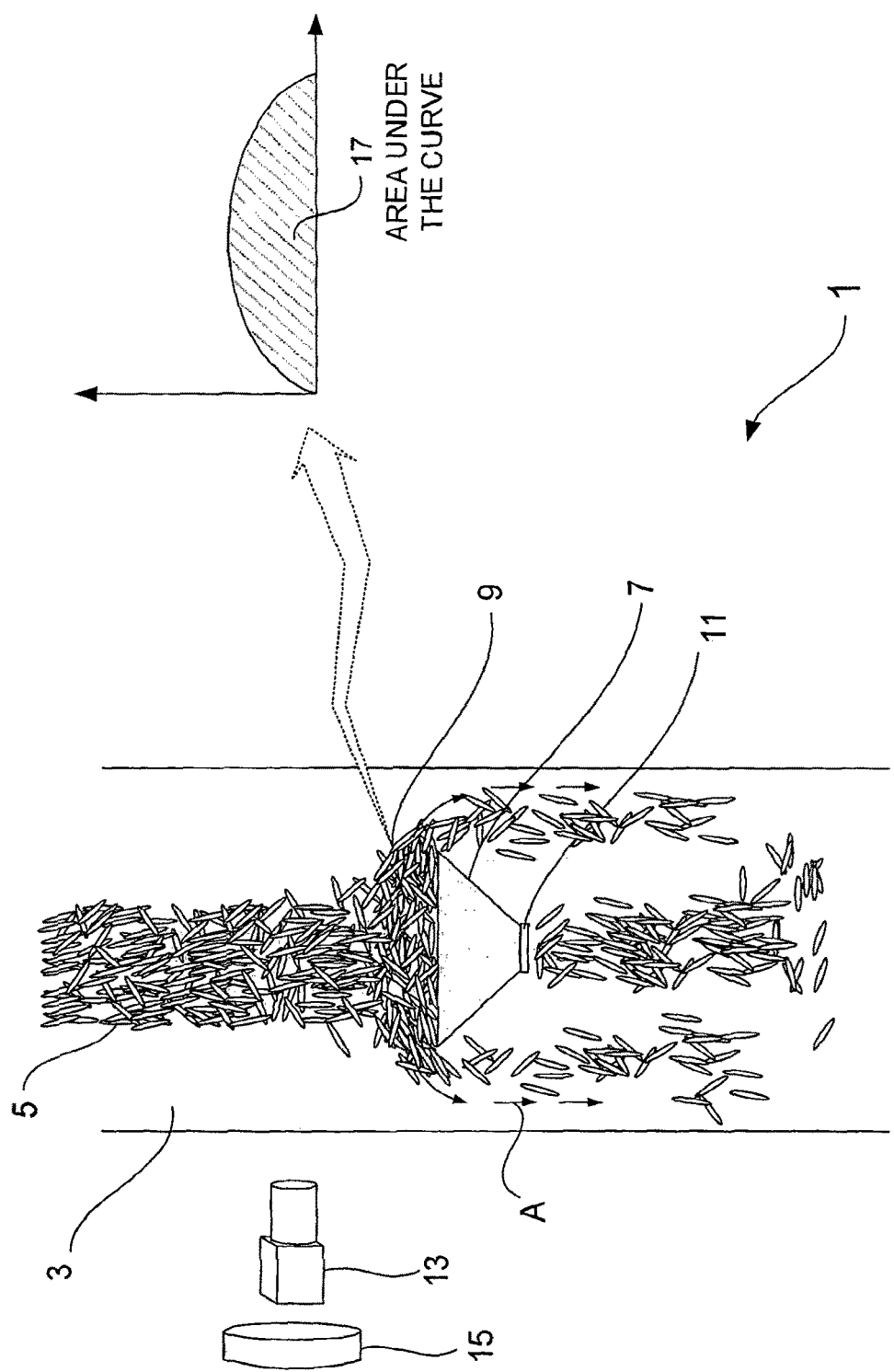
FIG. 1 is a schematic view showing an arrangement for measuring the smoothness of grains in accordance with a first embodiment of the invention.

FIG. 1 is a schematic view showing an arrangement for measuring the smoothness of grains 1 in accordance with a first embodiment of the invention. A channel 3 is provided for supplying grains 5, especially rice grains. The channel 3 has a vertical orientation in FIG. 1 with the grain 5 supplied from the upper side through the channel 3. The direction of movement of the grains 5 is schematically indicated by arrows A. An obstacle 7 is arranged in the channel 3. The obstacle 7 has the form of a hopper in this embodiment. Grains 5 falling on the obstacle 7 will slow down so that the flow of grains 5 forms a heap 9 on the obstacle 7. The obstacle 7 in this embodiment has an outlet 11 to allow grains 5 to pass through the obstacle 7. The outlet 11 is formed as a hole at the bottom of the obstacle 7, which is built as a hopper according to the first embodiment. Grains 5 can pass continuously through the outlet 11. Thus, the heap 9 of grains 5 is steadily renewed by supplying grains 5 from the upper side of the obstacle 7 and discharging grains 5 through the outlet 11.

An image capturing device 13 is arranged facing the obstacle 7. In FIG. 1 it is located to the left hand side of the obstacle 7. The image capturing device 13 according to the first embodiment is a digital camera. The image capturing device 13 is arranged to capture an image of the heap 9. Seen from the side as projection like in the captured image, the heap 9 forms with its upper surface a curve 17. The area under the curve 17 indicates the degree of smoothness of the grains. The larger the area under the curve 17 relate to lower degree of smoothness and the smaller the area under the curve 17 relate to higher degree of smoothness. The form of the curve 17 can be adequately analyzed showing the degree of smoothness, too. If the curve 17 has more steep sections it indicates less smoothness of the grains 5. A light source 15 is provided for radiating light on the grains 5, especially the heap 9. Thus, the light source 15 can help to improve the image capturing conditions for the image capturing device 13.

Figure 2:
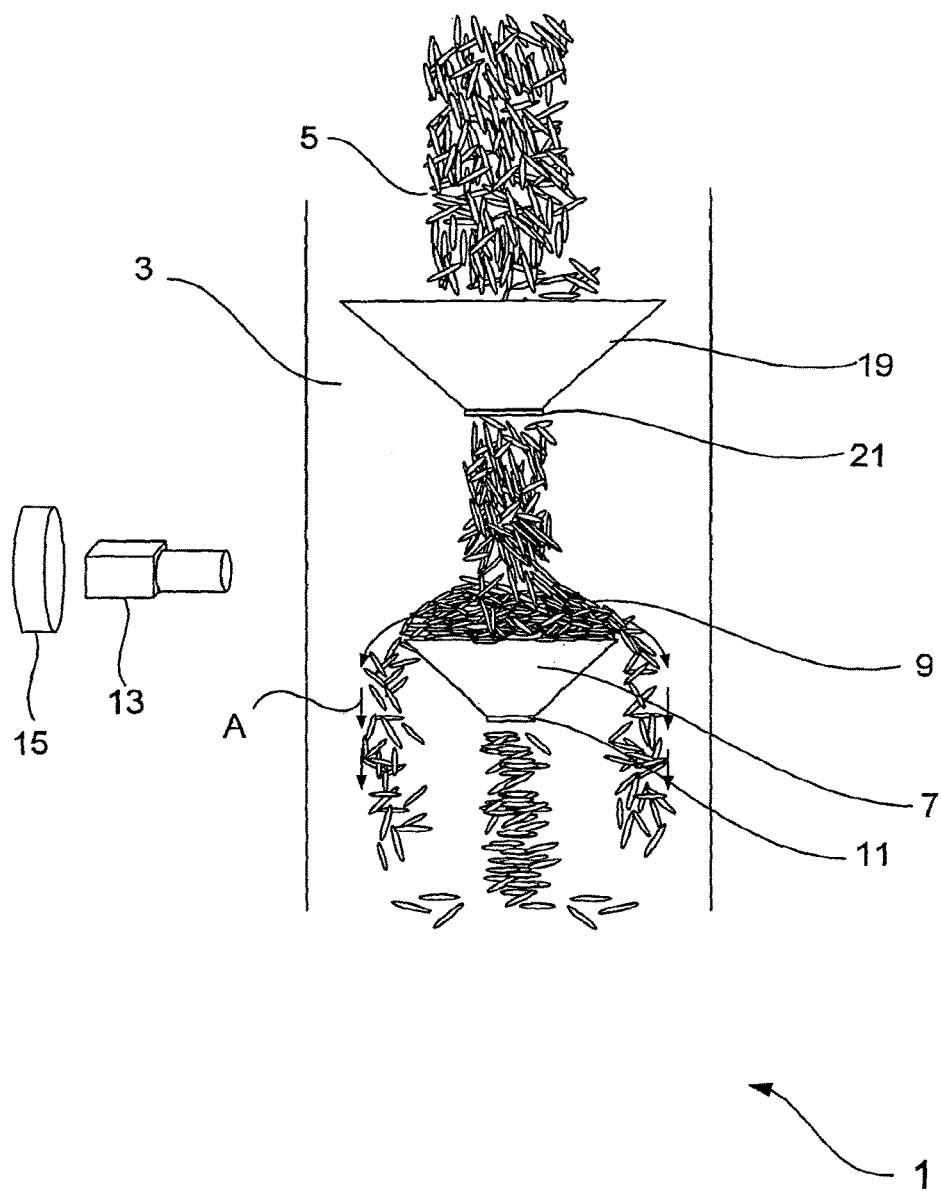
FIG. 2 is a schematic view showing an arrangement for measuring the smoothness of grains in accordance with a second embodiment of the invention.

FIG. 2 is a schematic view showing an arrangement for measuring the smoothness of grains 1 in accordance with a second embodiment of the invention. As in the first embodiment a channel 3 for supplying grains 5, especially rice grains, is provided. An obstacle 7 formed as a hopper is arranged in the channel 3. The obstacle 7 has an outlet for discharging grains 5 from the obstacle 7. Grains 5, falling on the obstacle 7, form a heap 9 on the obstacle 7. The heap 9 of grains 5 will not exceed a definite height because of the grains 5 running down the heap 9. The form and size of the heap 9 indicates the smoothness of the grains 5. If the grains 5 are more smooth they run more easily down the heap 9. Therefore the heap 9 is prevented from exceeding a height that depends on the smoothness of the grains 5. If the grains 5 are less smooth they intend more to stick together due to their friction and the heap 5 will build higher.

As in the first embodiment an image capturing device 13 is provided beside the heap 9 to capture an image of the heap 9. The curve 17 of the heap 9 seen as side elevation indicates the smoothness of the grains 5 as described with respect to the first embodiment. A light source 15 is arranged to improve the light conditions in the channel for capturing the image of the heap 9.

Additional to the first embodiment in the second embodiment a collecting element 19, according to this embodiment formed as a hopper, is arranged above of the obstacle 7. The collecting element 19 collects grains 5 from the channel 3 and leads the grains 5 on the obstacle 7. By this measure the grains 5 can be led to the obstacle 7 with definite velocity largely independent of the grain transporting speed in the channel 3. That prevents influence of the speed of the grains 5 in the channel 3 on the building of the heap 9. The influence of a high impact speed of grains 5 on the obstacle 7 and resulting erosions on the building heap 9 can be prevented. The collecting element 19 is formed according to the second embodiment as a hopper, collecting grains 5 from the channel 3 and having a discharge port 21 for discharging the grains 5 on the obstacle 7. Therefore the discharge port 21 is located above the obstacle 7. The collecting element 19 farther shields the obstacle 7 in vertical direction from the flow of grains 5 and thus prevents grains 5 from falling with unreduced velocity directly on the obstacle 7. Therefore the diameter of the collecting element 19 according to the second embodiment is equal or larger than the diameter of the obstacle 7. The second embodiment offers the advantage of a very definite grain supply to the obstacle 7.

In the foregoing detailed description of embodiments of the invention, various features are grouped together in a single embodiment for the purpose of streamlining the disclosure. This method of disclosure is not to be interpreted as reflecting an intention that the claimed embodiments of the invention require more features than are expressly recited in each claim. Rather, as the following claims reflect, inventive subject matter lies in less than all features of a single disclosed embodiment. Thus, the following claims are hereby incorporated into the detailed description of embodiments of the invention, with each claim standing on its own as a separate embodiment.

It is understood that the above description is intended to be illustrative, and not restrictive. It is intended to cover all alternatives, modifications and equivalents as may be included within the spirit and scope of the invention as defined in the appended claims. Many other embodiments will be apparent to those of skill in the art upon reviewing the above description. The scope of the invention should, therefore, be determined with reference to the appended claims, along with the full scope of equivalents to which such claims are entitled.

We claim:

1. An arrangement for measuring the smoothness of grains, comprising:
   a vertical channel for supplying grains, especially rice grains;
   a vessel arranged at the channel to slow down grains falling on the vessel, so that the flow of grains forms a heap on the vessel; and
   a camera placed facing the vessel;
   wherein the camera is arranged to capture an image of the heap, and wherein the area under the curve of the captured heap image indicates a degree of smoothness of the grains.

2. The arrangement of claim 1, wherein the vessel has a discharge port, especially a hole, as outlet for the grains.

3. The arrangement of claim 1, wherein the vessel is formed as a hopper for collecting the grains.

4. The arrangement of claim 1, wherein the captured image of the heap is proportional to the degree of smoothness of the grains, the larger the area under the heap curve indicating a lower degree of smoothness and the smaller the area under the heap curve indicating a higher degree of smoothness.

5. The arrangement of claim 1, wherein the camera is a digital camera.

6. The arrangement of claim 1, further comprising:
   a light source for radiating light on the grains, especially the grains lying on the vessel.

7. The arrangement of claim 1, further comprising:
   a collecting element, especially a hopper, with a discharge port positioned above the vessel.

8. The arrangement of claim 1, wherein the vertical channel is built as a bypass of a main channel for conveying the grains.

9. A method for measuring the smoothness of grains, comprising:
   supplying grains, especially rice grains, through a vertical channel;
   slowing down falling down grains by a vessel, so that the flow of grains forms a heap on the vessel;
   capturing an image of the heap with a camera;
   determining the area under the curve of the captured heap image, wherein the area of the curve is used to indicate a degree of smoothness of the grains, the larger area under the heap curve indicating a lower degree of smoothness and the smaller the area under the heap curve indicating a higher degree of smoothness or analyzing the form of the curve.

10. The method according to claim 9, wherein a course of the heap curve is used to indicate the degree of smoothness of the grains, steeper sections of the curve indicating a lower degree of smoothness and less steep sections indicating a higher degree of smoothness of the grain.

11. The method according to claim 9, wherein the area covered by the curve is determined by a CPU connected to the camera.

12. The method according to claim 9, wherein grain is collected from the vertical channel by a collecting element, especially a hopper, and discharged from the collecting element on the vessel via a discharge port of the collecting element.

\* \* \* \* \*